(12) United States Patent
Tewarson

(10) Patent No.: US 8,181,504 B2
(45) Date of Patent: May 22, 2012

(54) SMOKE EVALUATING DEVICE AND RELATED METHOD

(75) Inventor: Archibald Tewarson, Newton Center, MA (US)

(73) Assignee: Factory Mutual Insurance Company, Johnston, RI (US)

( * ) Notice: Subject to any disclaimer, the term of this patent is extended or adjusted under 35 U.S.C. 154(b) by 627 days.

(21) Appl. No.: 12/372,912

(22) Filed: Feb. 18, 2009

(65) Prior Publication Data

US 2010/0206043 A1  Aug. 19, 2010

(51) Int. Cl.
*G01N 3/32* (2006.01)
*G01N 1/22* (2006.01)

(52) U.S. Cl. ............ 73/23.41; 73/28.01; 73/28.04; 73/863.23; 73/863.31; 73/863.51; 73/863.53; 73/863.61; 73/863.83; 73/864.23; 73/864.33; 73/865.5; 73/865.6

(58) Field of Classification Search ............ 73/28.01, 73/28.04, 863.23, 863.31, 863.51, 863.53, 73/863.61, 863.83, 864.34, 865.5, 865.6, 73/23.41
See application file for complete search history.

(56) References Cited

U.S. PATENT DOCUMENTS

| | | | |
|---|---|---|---|
| 2,743,995 A | 5/1956 | Sherrick | |
| 3,694,157 A | 9/1972 | Koch et al. | |
| 3,765,247 A | 10/1973 | Riggs | |
| 3,904,368 A | 9/1975 | Takeyama et al. | |
| 4,073,619 A | 2/1978 | Lawson | |
| 4,090,392 A | 5/1978 | Smith et al. | |
| 4,182,959 A | 1/1980 | MacCleary et al. | |
| 4,600,695 A * | 7/1986 | Cummings et al. | 436/2 |
| 4,654,058 A | 3/1987 | Schober et al. | |
| 4,705,669 A | 11/1987 | Tsuji et al. | |
| 4,789,524 A | 12/1988 | Rio et al. | |
| 5,369,981 A | 12/1994 | Merz et al. | |
| 5,644,071 A | 7/1997 | Wagner | |
| 5,717,147 A | 2/1998 | Basch et al. | |
| 5,898,114 A | 4/1999 | Basch et al. | |
| 6,332,349 B1 * | 12/2001 | Poynot | 73/23.2 |
| 6,736,883 B2 | 5/2004 | Sjostrom et al. | |
| 6,779,413 B1 * | 8/2004 | Heskestad | 73/865.6 |
| 7,029,920 B2 | 4/2006 | Lanier et al. | |
| 7,100,423 B2 | 9/2006 | Trenholm | |

* cited by examiner

*Primary Examiner* — Daniel Larkin
(74) *Attorney, Agent, or Firm* — Venable LLP; Clifton E. McCann; Steven J. Schwarz

(57) ABSTRACT

A smoke evaluation device includes a manifold in fluid communication with a source of smoke, and a first sampling line and a second sampling line in fluid communication with the manifold. The first sampling line and the second sampling line are arranged to convey parallel smoke flows. A first filter station is located in the first sampling line, and is adapted to support a filter paper in fluid communication with the smoke. A first circuit board station is located in the second sampling line, and is adapted to support a circuit board in fluid communication with the smoke.

18 Claims, 1 Drawing Sheet

SMOKE EVALUATING DEVICE AND RELATED METHOD

TECHNICAL FIELD

The present invention relates to a method and apparatus for evaluating the smoke damaging properties of various types and/or sources of smoke.

BACKGROUND

According to known techniques, the optical density and corrosive properties of smoke are measured separately. For example, these measurements may be taken in the exhaust products of a fire directly, or by collecting the exhaust products in a vessel for subsequent evaluation. The optical density of the smoke typically relates to the visibility of the smoke. The corrosiveness of the smoke typically relates to its ability to impart smoke damage. However, neither of these measurements relate to certain aspects of the damage expected from the smoke in smoke sensitive occupancies (e.g., residential or commercial buildings). For example, these measurements do not indicate the level of smoke damage caused due to malodor and/or staining. These measurements also fail to indicate the level of damage (e.g., malfunction) imparted to electrical and/or electronic appliances or other items due to the smoke.

SUMMARY

According to an illustrative embodiment, a smoke evaluation device comprises: a manifold in fluid communication with a source of smoke; a first sampling line and a second sampling line in fluid communication with the manifold, the first sampling line and the second sampling line being arranged to convey parallel smoke flows; a first filter station located in the first sampling line, the first filter station adapted to support a filter paper in fluid communication with the smoke; and a first circuit board station located in the second sampling line, the first circuit board station adapted to support a circuit board in fluid communication with the smoke.

According to another illustrative embodiment, a method of evaluating smoke comprises: drawing smoke from a first smoke source into a manifold; dividing the smoke into a first parallel stream and a second parallel stream; capturing smoke particulates on a first filter paper located in contact with the first parallel stream; exposing a first circuit board to the second parallel stream; analyzing the smoke particulates on the first filter paper; and measuring a property of the first circuit board.

Further objectives and advantages, as well as the structure and function of illustrative embodiments, will become apparent from a consideration of the description and drawings.

BRIEF DESCRIPTION OF THE DRAWINGS

The foregoing and other features and advantages of the invention will be apparent from the following, more particular description, as illustrated in the accompanying drawings wherein like reference numbers generally indicate identical, functionally similar, and/or structurally similar elements.

DETAILED DESCRIPTION

Figure 1:
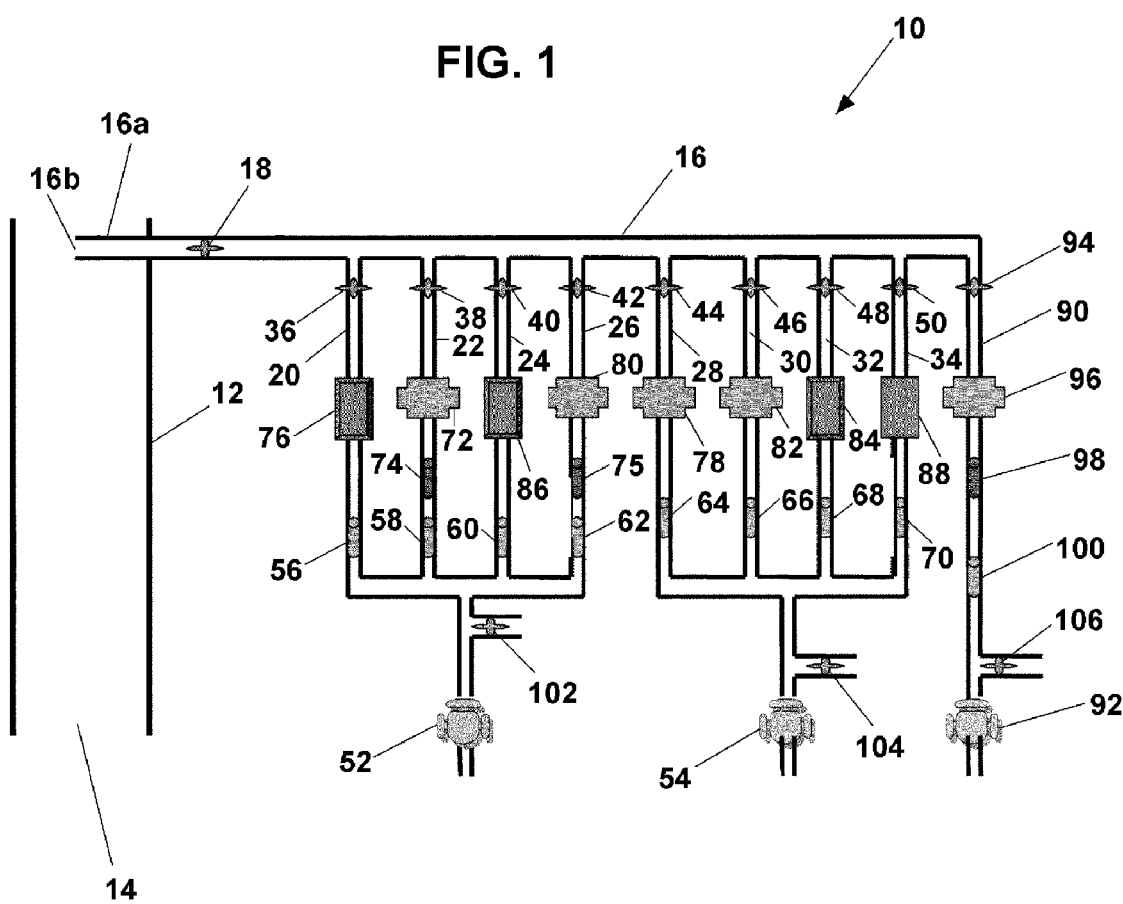
FIG. 1 is a schematic representation of a first illustrative embodiment of a smoke sampler according to the present invention.

Embodiments of the invention are discussed in detail below. In describing embodiments, specific terminology is employed for the sake of clarity. However, the invention is not intended to be limited to the specific terminology so selected. While specific embodiments are discussed, it should be understood that this is done for illustration purposes only. A person skilled in the relevant art will recognize that other components and configurations can be used without departing from the spirit and scope of the invention.

The present invention relates to a method and apparatus that can be used to evaluate and/or classify the smoke damaging properties of smoke emanating from various different fire sources (e.g., commodities such as paper rolls or stacks of cardboard, manufacturing items such as equipment or raw materials, construction materials such as wood and drywall, and household items such as furniture or consumer electronics). The method and apparatus can be used to quantify smoke properties for the assessment of smoke damage caused by, for example, malodor, corrosion, stain, and/or malfunction of electrical and/or electronic components.

According to an illustrative embodiment, the chemical composition of smoke, its ability to impart malodor and/or stain to exposed surfaces, and/or its ability to corrode or damage electronic and/or electrical circuits can be quantified simultaneously, for example, using test fires of any size. The test fires can be performed in the presence or absence of fire suppressing agents. According to an illustrative embodiment, the method and apparatus can provide better assessment of the loss expectancy associated with non-thermal smoke damage, for example, to various types of properties having various types of contents.

Referring to FIG. 1, an illustrative smoke evaluation device 10 is depicted schematically. The device 10 can be attached to a smoke duct 12, through which the smoke from a test fire flows. The smoke duct 12 can include an open input region 14, such as a port, to receive, among other things, smoke or a smoke-air mixture (referred to generally herein as "smoke"), for example, from a test fire. The smoke duct 12 can have a generally duct-like, tubular structure, and can be constructed from various types of inert materials, such as stainless steel, and can have various shapes and dimensions based on, for example, the size and configuration of the test fire.

A manifold 16 can be in fluid communication with the smoke duct 12. For example, an open end of the manifold 16 can be connected to an opening in the smoke duct 12. Additionally or alternatively, a probe portion 16a of the manifold can extend into the smoke duct 12 and have an open end 16b located within the fire duct 12, as shown in FIG. 1. The probe portion 16a can provide for isokinetic sampling of the flow in the smoke duct 12. According to an illustrative embodiment, the manifold 16 can comprise a tube having a diameter of between about ¼" and about 1", and more preferably between about ½" and ¾", however, other shapes and dimensions are possible. According to an illustrative embodiment, the manifold 16 can comprise a tube of fire hardened material, such as silicon, Teflon®, or PFA, and all or some of probe portion 16a can comprise a metal tube, for example, stainless steel. Alternatively, the manifold 16 and probe portion 16a can be formed of the same material. According to an illustrative embodiment, the probe portion 16a can have a diameter of between about 1A" and about 1", more preferably about ¾", however, other shapes and dimensions are possible.

A valve 18 can be provided in the manifold 16 to selectively limit or block the flow of smoke to the manifold 16 and/or other downstream components. Valve 18 can comprise any number of open/close valves known in the art, such as a needle valve, and can be of the manual or automatic type. According to an illustrative embodiment, valve 18 can comprise a Swagelok L-Series #SS-4L valve made by the Swagelok Company, located at 29500 Solon Road, Solon, Ohio 44139.

A plurality of sampling conduits or lines 20-34, such as pipes, hoses, tubes, or other similar structures, can branch off from the manifold 16. The sampling lines 20-34 can be arranged to carry parallel flows of smoke. One of ordinary skill in the art will appreciate that the sampling lines 20-34 are not necessarily limited to being parallel to one another in a geometric sense, although, such a configuration is possible, as shown. One or more of the sampling lines 20-34 can include a valve located proximate its upper end (as seen in FIG. 1), for example, to selectively block smoke flow through the respective sampling line. According to the illustrative embodiment shown in FIG. 1, a valve 36-50 can be located in each sampling line 20-34, respectively, although other configurations are possible. Each valve 36-50 can comprise any number of open/close valves known in the art, such as needle valves, and can be of the manual or automatic type. According to an illustrative embodiment, the valves 36-50 can each comprise a Swagelok L-Series #SS-4L valve made by the Swagelok Company, located at 29500 Solon Road, Solon, Ohio 44139.

One or more pumps can be provided to draw air through the sampling lines 20-34. For example, a first pump 52 can be provided to draw air through sampling lines 20-26, collectively, and a second pump 54 can be provided to draw air through sampling lines 28-34, collectively. The pumps 52 and 54 can be variable speed pumps. Alternatively, the pumps 52 and 54 can be fixed speed pumps. According to an illustrative embodiment, pumps 52 and 54 both have capacities of equal to or greater than about 250 liters/minute, however, other configurations are possible. According to an illustrative embodiment, the pumps 52, 54 can each comprise a Gast #0823V131QSG608X manufactured by Gast Manufacturing, Inc., located at P.O. Box 97, Benton Harbor, Mich. 49023-0097. Alternatively, the pumps 52, 54 can each comprise a Grainger #4F741 manufactured by W.W. Grainger, Inc., located at 100 Grainger Parkway, Lake Forest, Ill. 60045-5201. The first pump 52 and second pump 54 can be operated independently of one another, for example, at different speeds. Accordingly, the flow rate through sampling lines 20-26 can be set at a different value than the flow rate through sampling lines 28-34 via the relative speed of pumps 52, 54.

A flowmeter can be provided in one or more of the sampling lines 20-34, for example, to measure the flow rate through the respective line. According to the illustrative embodiment shown in FIG. 1, a flowmeter 56-70 can be located in each sampling line 20-34, respectively, although other configurations are possible. According to an exemplary embodiment, one or more of the flowmeters 56-70 can comprise a Dwyer #RMB-52D-SSV-BPG made by Dwyer Instruments Inc., located at P.O. Box 373, 102 Indiana Highway 212, Michigan City, Ind. 46361. Alternatively, one or more of the flowmeters 56-70 can comprise a Dwyer #VFB-65-SSBV made by Dwyer Instruments Inc.

One or more of the flowmeters 56-70, if provided, can be used to monitor the flow rate through the respective sampling line that it is located in, and to adjust the pumping rate of the corresponding pump 52, 54, as will be described in more detail below.

One or more filter stations can be located in the sampling lines. For example, a first filter station 72 can be located in sampling line 22. Filter station 72 can include an interior chamber that can removably support a filter in contact with the smoke passing through the sampling line 22. According to an illustrative embodiment, the filter can comprise a quartz filter, such as a No. AQFA04700 filter made by Millipore, located at 290 Concord Road, Billerica, Mass. 01821. Alternatively, the filter can comprise cellulosic-type filters, or filter papers. Filter station 72 can include two or more components that open/close with respect to one another to allow introduction and removal of the filter from the filter station 72. According to an illustrative embodiment, the interior chamber of the filter station 72 can have a diameter of between about ⅛" and about 1", however, other configurations are possible. According to an illustrative embodiment, the filter station can be a stainless steel filter station manufactured by Apex Instruments, Inc., located at 204 Technology Park Lane, Fuquay-Varina, N.C. 27526. When the smoke evaluation device 10 is in use, smoke can be drawn through the sampling line 22 and through the filter located in the first filter station 72.

The filters can capture particulates in the smoke for later testing and analysis. For example, particulates deposited on the filters can be weighed and analyzed using gas chromatography, mass spectrometry, and/or ion chromatography.

Passive sampling tubes can also be located in one or more of the sampling lines. For example, a passive sampling tube 74 can be located in sampling line 22, for example, downstream of the first filter station 72. The passive sampling tube 74 can removably support an adsorbent material, such as Tenax, in contact with the smoke flowing through the sampling line 22. The adsorbent material can comprise, for example, ~0.02 g Tenax TA/tubes manufactured by PerkinElmer Life and Analytical Sciences, located at 710 Bridgeport Avenue, Shelton, Conn. 06484-4794. Tenax TA is a resin material of 2, 6-diphenyl-p-phenlyne oxide having a mesh size of 35/60. The adsorbent material can collect non-particulate matter from the smoke, which can be later analyzed, for example, tested for the presence of volatile organic compounds. Non-particulates adsorbed on the adsorbent material can be analyzed, for example, using gas chromatography and/or mass spectrometry.

A second passive sampling tube 75, and accompanying adsorbent material, can be located in the second sampling line 26, for example, downstream of the filter station 80. The presence of multiple, similar passive sampling tubes can allow for comparison between similar tests, and/or a determination of the accuracy of the tests.

Circuit board resistance target stations can be located in one or more of the sampling lines. For example, a first circuit board station 76 can be located in sampling line 20. The first circuit board station 76 can removably support a circuit board or other small electric or electronic device inside a chamber in contact with the smoke flowing through the line 20. According to an illustrative embodiment, the circuit board stations can comprise 90 mm PFA filter holders, for example, model 401-23-90-40-23-1 made by Savillex Corporation, located at 6133 Baker Road, Minnetonka, Minn. 55345-5910. Filters, such as filter papers, can be located in the circuit board stations, for example, 90 mm PTFE filter papers made by Savillex Corporation. The circuit board stations can support leakage currents, for example, from small electrical or electronic devices, corrosion probes and metal coupons, which are placed on top of the filters inside the stations. As shown in FIG. 1, a second circuit board station 86 can be located in sampling line 24.

A second filter station 78 can be located in sampling line 28. Second filter station 78 can support a filter, such as a filter paper, in contact with the smoke stream through line 28, and can have the same or similar structure as the first filter station 72, described above. Third and fourth filter stations 80, 82 can be located in sampling lines 26 and 30, respectively. Third and fourth filter stations 80, 82 can each support a filter in contact with the smoke stream through the respective sampling line 26, 30, and can each have the same or similar structure as the first filter station 72, described above. The presence of multiple, similar filter stations can allow for collection of smoke at different fire stages.

A second circuit board station 86 can be located in sampling line 24. Second circuit board station 86 can support a circuit board, or other electronic device, in contact with the smoke flowing through sampling line 24, and can have the same or similar structure as the first circuit board station 76, described above.

Third and fourth circuit board stations 84, 88 can be located in sampling lines 32 and 34, respectively. The third and fourth circuit board stations 84, 88 can each support a circuit board, or other electronic device, in contact with the smoke stream through the respective sampling line 32, 34, and can each have the same or similar structure as the first circuit board station 76, described above. The presence of multiple, similar circuit board stations can allow for comparison between similar tests, and/or a determination of the accuracy of the tests.

The first and second pumps 52, 54, described above, can be operated independently from one another, for example, at different speeds. For example, first pump 52 can operate at about 9 liters/minute, while second pump 54 can operate at about 18 liters/minute. Accordingly, the flow rate through the sampling lines 20-26 can be different than the flow rate through the sampling lines 28-34.

Alternatively, the first and second pumps 52, 54 can be operated at the same speed, for example, approximately 250 liters/minute. According to this embodiment, the flow through sampling lines 20-34, 90, can be adjusted using the valves 102, 104, and/or 106. According to an illustrative embodiment, the flow through sampling lines 20, 24, 28, 30, 32, and 34 is set to approximately 4.5 liters/minute, and the flow through sampling lines 22 and 26 is set to approximately 0.1 liters/minute.

By altering flow rates, it can be possible to use a combination of filter papers and Tenax tubes for the filters, as using higher flow rates for filter papers collects higher amounts of particulates, whereas using lower flow rates for Tenax tubes avoids over saturation of the Tenax by non-particulates.

The smoke evaluation device 10 can also include a bypass line 90. The bypass line 90 can connect to the manifold 16, and bypass the various sampling lines 20-34, for example, to rapidly sample smoke. The bypass line 90 can include a bypass pump 92 to draw smoke (or an air/smoke mixture) through the bypass line. The bypass pump 92 can have a capacity of at least about 54 liters/minute, however, other capacities are possible. According to an illustrative embodiment, the pump 92 can comprise a Gast #DOA-P703-PB manufactured by Gast Manufacturing, Inc., or a Grainger #4Z024 manufactured by W.W. Grainger, Inc. According to an illustrative embodiment, the pump 92 can operate at a speed of approximately 54 liters/minute, and the valve 106 can be adjusted to provide a flow rate in the bypass line 90 of approximately 4.5 liters/minute.

The bypass line 90 can also include a valve 94, filter station 96, passive sampling tube 98, and/or flowmeter 100, all of which can be the same or similar to those described previously. The filter station 96 and sampling tube 98 in the bypass line 90 can be used to obtain background information for particulates and non-particulates contained in the smoke. According to an illustrative embodiment, the bypass pump 92 can draw smoke through the bypass line 90 at about 4.5 liters/minute.

A valve 102 can be located between the set of sampling lines 20-26 and the first pump 52, and a valve 104 can be located between the set of sampling lines 28-34 and the second pump 54. A valve 106 can also be located in the bypass line 90 upstream of the bypass pump 92. Valves 102, 104, and 106 can be fully opened to rapidly cool pumps 52, 54, and 92, respectively.

Although not illustrated, a controller, such as a computer, programmable logic controller (PLC), or other electronic device can be used to automate the operation of the smoke evaluation device 10. For example, the controller may be in communication with one or more of the pumps 52, 54, 92. The controller may also be in communication with one or more of the valves 36-50, 94. The controller may also be in communication with one or more of the flowmeters 56-70, 100. The controller can be adapted to receive information from one or more of the flowmeters 56-70, 100 regarding the various flow rates in the device 10. The controller can be further adapted to compare the received flow rate information to the desired flow rates at various times and points in the operation of the device 10, and, based on this comparison, control the speed of the various pumps 52, 54, and 92, and/or adjust the position of the various valves 36-50, 94, to obtain the desired flow rates. One of ordinary skill in the art will understand that other types of control systems can be used to automate the operation of device 10. Further, one of ordinary skill in the art will understand that the device 10 can be operated manually, or by a combination of manual and automated processes.

Depending on the specific application, the smoke evaluation device 10 can have a single sampling line or multiple sampling lines. In addition, the smoke evaluation device 10 can have a single pump for all sampling lines, or multiple pumps (e.g., as shown in FIG. 1).

Illustrative methods of evaluating smoke will now be described in more detail with reference to FIG. 1. One of ordinary skill in the art will understand, however, that the following methods can additionally be practiced using devices other than the one shown in FIG. 1.

Referring to FIG. 1, an illustrative method of evaluating smoke can include drawing smoke from a first source, such as a test fire, through the smoke duct 12, for example, using one or more pumps 52, 54. The smoke can be divided into multiple parallel streams, for example eight streams, by directing it through multiple sampling lines 20-34. Additionally, the smoke can be divided into another stream that flows through a bypass line 90, for example, for background information on the smoke, or to prevent overheating the pumps 52, 54.

Various different test stations can be located in fluid contact with one or more of the streams, to allow various different fire stages to be analyzed. For example, smoke particulates can be captured in filters placed in contact with one or more of the smoke streams. According to an illustrative embodiment, shown in connection with FIG. 1, filter papers can be located in the fluid streams flowing through sampling lines 22, 26, 28, and 30, for example, by placing the filter papers in filter stations 72, 80, 78, and 82, respectively.

After subjecting the filters to the respective smoke streams for a desired amount of time (which may vary from filter station to filter station, or alternatively, may be the same for all filter stations), the filters can be removed from their filter stations 72, 80, 78, and 82, and analyzed. For example, the smoke particulates captured on the filters can be weighed. Additionally or alternatively, the smoke particulates can be vaporized and analyzed using electrochemical or other techniques, including gas chromatography (GC), mass spectroscopy (MS), and ion chromatography (IC), for example, to identify corrosive ions such as chloride, bromide, fluoride, and phosphate. The data from these analyses can be compared to literature information to quantify, for example, the malodor and/or stain properties of the smoke.

Printed circuit boards and the like can also be placed in contact with one or more of the smoke streams, for example, to test the effects of their exposure to the smoke. According to an illustrative embodiment, shown in connection with FIG. 1, printed circuit boards can be located in contact with the smoke streams via the circuit board test stations 76, 86, 84, and 88 located in sampling lines 20, 24, 32, and 34, respectively.

After subjecting the circuit boards to the respective smoke streams for a desired amount of time (which may vary from circuit board to circuit board, or alternatively, may be the same for all circuit boards), the circuit boards can be removed from their respective test stations 76, 86, 84, and 88, and analyzed. For example, each circuit board can be measured for its leakage current. According to an illustrative embodiment, one or more of the circuit boards can be placed in a humidity chamber after removal from its test station, and tested for its leakage current, using known techniques. The one or more circuit boards can then be washed, replaced in the humidity chamber, and re-tested for its leakage current. The measured leakage current values can be used to quantify the damaging properties of the smoke to, among other things, electrical and electronic components.

Filters, such as filter papers or Tenax tubes, can also be located in one or more of the circuit board test stations 76, 86, 84, and 88, for example, downstream of the circuit boards. These filter papers can also collect smoke particulates, for later analysis.

Non-particulate components of the smoke can also be captured and analyzed. With reference to FIG. 1, the smoke can be drawn through sampling tubes containing an adsorbent material, such as Tenax. The sampling tubes 74, 75 can be located in sampling lines 22 and 26, for example, downstream of filter stations 72, 80, and can collect, among other things, volatile organic compounds (VOCs) contained in the smoke.

After the adsorbent material collects non-particulate components of the smoke for a desired amount of time (which may vary from sampling tube to sampling tube, or alternatively, may be the same for all sampling tubes), the adsorbent material can be removed from the respective sampling tube 74, 75, and analyzed. For example, the non-particulate material can be tested for VOCs, using, for example, GC or MS. This data can be used to quantify the malodor and stain properties of the smoke.

The smoke collection performed in the above-described filter papers, adsorbent materials, and circuit boards can all be performed at the same time, or alternatively, can be performed as separate, discrete steps. In addition, the flow rate of each smoke stream can be varied, for example, by adjusting the pump speed and/or adjusting the position of the valve located in the respective sampling line. Referring to FIG. 1, for example, the flow rate of pumps 52, 54, and 92 can be adjusted in response to changes in the flow rate of smoke in the sampling duct 12 (based, for example, on changes in the test fire), in order to maintain isokinetic sampling of the smoke.

Additionally or alternatively, the flow rates can be varied from one stream to another, for example, for collection of the smoke at different sampling rates. Referring to FIG. 1, according to an illustrative embodiment, the first pump 52 can be operated at a flow rate of approximately 34 liters/minute. Valves 36, 38 can be adjusted to provide smoke flow rates of approximately 1 to 2 liters/minute in sampling lines 20 and 22, and valves 40, 42 can be adjusted to provide smoke flow rates of approximately 15 liters/minute in sampling lines 24 and 26. Still referring to FIG. 1, according to an illustrative embodiment, the second pump 54 can be operated at a flow rate of approximately 60 liters/minute, and valves 44-50 can be adjusted to provide smoke flow rates of approximately 15 liters/minute in sampling lines 28-34, respectively. According to an illustrative embodiment, the bypass pump 92 can be operated at a flow rate of approximately 15 liters/minute. According to another illustrative embodiment, the flow rates through lines 20-34 can all be approximately 3-5 liters/minute, and more specifically, approximately 4 liters/minute, although other configurations are possible.

The embodiments illustrated and discussed in this specification are intended only to teach those skilled in the art the best way known to the inventors to make and use the invention. Nothing in this specification should be considered as limiting the scope of the present invention. All examples presented are representative and non-limiting. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

What is claimed is:

1. A smoke evaluation device, comprising:
    a manifold in fluid communication with a source of smoke;
    a first sampling line and a second sampling line in fluid communication with the manifold, the first sampling line and the second sampling line being arranged to convey parallel smoke flows;
    a first filter station located in the first sampling line, the first filter station adapted to support a filter in fluid communication with the smoke;
    a first circuit board station located in the second sampling line, the first circuit board station adapted to support a circuit board in fluid communication with the smoke; and
    a passive sampling tube located in the first sampling line, the passive sampling tube adapted to support an adsorbent material in fluid communication with the smoke.

2. The smoke evaluation device of claim 1 wherein the passive sampling tube is located downstream from the first filter station.

3. The smoke evaluation device of claim 1, further comprising:
    a first flow meter located in the first sampling line; and
    a second flow meter located in the second sampling line.

4. The smoke evaluation device of claim 1, further comprising:
    a first pump adapted to draw smoke through the first sampling line and the second sampling line.

5. The smoke evaluation device of claim 1, further comprising a bypass line in fluid communication with the manifold.

6. A smoke evaluation device, comprising:
    a manifold in fluid communication with a source of smoke;
    a first sampling line and a second sampling line in fluid communication with the manifold, the first sampling line and the second sampling line being arranged to convey parallel smoke flows;
    a first filter station located in the first sampling line, the first filter station adapted to support a filter in fluid communication with the smoke; and
    a first circuit board station located in the second sampling line, the first circuit board station adapted to support a circuit board in fluid communication with the smoke, wherein the first circuit board station is adapted to support a filter downstream of the circuit board.

7. A smoke evaluation device, comprising:
a manifold in fluid communication with a source of smoke;
a first sampling line and a second sampling line in fluid communication with the manifold, the first sampling line and the second sampling line being arranged to convey parallel smoke flows;
a first filter station located in the first sampling line, the first filter station adapted to support a filter in fluid communication with the smoke;
a first circuit board station located in the second sampling line, the first circuit board station adapted to support a circuit board in fluid communication with the smoke;
a first pump adapted to draw smoke through the first sampling line and the second sampling line;
a third sampling line and a fourth sampling line in fluid communication with the manifold, the first sampling line, second sampling line, third sampling line, and fourth sampling line being arranged to convey parallel smoke flows; and
a second pump adapted to draw smoke through the second sampling line and the third sampling line, wherein the first and second pumps are operable to draw smoke at different flow rates from one another.

8. The smoke evaluation device of claim 7, further comprising:
a second filter station located in the third sampling line, the second filter station adapted to support a filter in fluid communication with the smoke; and
a second circuit board station located in the fourth sampling line, the second circuit board station adapted to support a circuit board in fluid communication with the smoke.

9. A method of evaluating smoke, comprising:
drawing smoke from a first smoke source into a manifold;
dividing the smoke into a first parallel stream and a second parallel stream;
capturing smoke particulates on a first filter located in contact with the first parallel stream;
exposing a first circuit board to the second parallel stream;
analyzing the smoke particulates on the first filter;
measuring a property of the first circuit board;
dividing the smoke into a third parallel stream and a fourth parallel stream;
capturing smoke particulates on a second filter located in contact with the third parallel stream;
exposing a second circuit board to the fourth parallel stream;
analyzing the smoke particulates on the second filter; and
measuring a property of the second circuit board.

10. The method of claim 9, further comprising:
capturing non-particulate components of the smoke in a sampling tube located in fluid communication with the first parallel stream downstream of the first filter; and
analyzing the non-particulate components.

11. The method of claim 10, wherein analyzing the non-particulate components comprises testing for volatile organic compounds in the non-particulate components.

12. The method of claim 10, wherein analyzing the non-particulate components comprises performing gas chromatography and/or mass spectrography on the non-particulate components.

13. The method of claim 9, further comprising:
drawing the first parallel stream and the second parallel stream at a first flow rate; and
drawing the third parallel stream and the fourth parallel stream at a second flow rate;
wherein the first flow rate is different than the second flow rate.

14. A method of evaluating smoke, comprising:
drawing smoke from a first smoke source into a manifold;
dividing the smoke into a first parallel stream and a second parallel stream;
capturing smoke particulates on a first filter located in contact with the first parallel stream;
exposing a first circuit board to the second parallel stream;
analyzing the smoke particulates on the first filter;
measuring a property of the first circuit board;
capturing smoke particulates on an additional filter located in contact with the second parallel stream downstream of the circuit board; and
analyzing the smoke particulates on the additional filter.

15. A method of evaluating smoke, comprising:
drawing smoke from a first smoke source into a manifold;
dividing the smoke into a first parallel stream and a second parallel stream;
capturing smoke particulates on a first filter located in contact with the first parallel stream;
exposing a first circuit board to the second parallel stream;
analyzing the smoke particulates on the first filter;
measuring a property of the first circuit board; and
adjusting a flow rate of the first and second parallel streams in response to changes in flow rate of the smoke in the duct.

16. A method of evaluating smoke, comprising:
drawing smoke from a first smoke source into a manifold;
dividing the smoke into a first parallel stream and a second parallel stream;
capturing smoke particulates on a first filter located in contact with the first parallel stream;
exposing a first circuit board to the second parallel stream;
analyzing the smoke particulates on the first filter; and
measuring a property of the first circuit board, wherein analyzing the smoke particulates on the first filter comprises performing gas chromatography and/or mass spectrography and/or ion chromatography on the smoke particulates.

17. A method of evaluating smoke, comprising:
drawing smoke from a first smoke source into a manifold;
dividing the smoke into a first parallel stream and a second parallel stream;
capturing smoke particulates on a first filter located in contact with the first parallel stream;
exposing a first circuit board to the second parallel stream;
analyzing the smoke particulates on the first filter; and
measuring a property of the first circuit board, wherein measuring a property of the first circuit board comprises placing the first circuit board in a humidity chamber and measuring the leakage current of the first circuit board.

18. The method of claim 17, further comprising:
washing the first circuit board before measuring the leakage current.

* * * * *